United States Patent

Nowak et al.

[11] Patent Number: 5,824,720
[45] Date of Patent: Oct. 20, 1998

[54] FLUORIDE-RELEASING COMPOSITE MATERIALS

[75] Inventors: Reinhold Nowak, Adelshofen; Erich Wanek, Kaufering; Bernd Gangnus, Herrsching, all of Germany

[73] Assignee: Thera Patent GmbH & Co. KG Gesellschaft für industrielle Schutzrechte, Seefeld, Germany

[21] Appl. No.: 574,851

[22] Filed: Dec. 19, 1995

[30] Foreign Application Priority Data

Dec. 19, 1994 [DE] Germany .......................... 44 45 266.7

[51] Int. Cl.$^6$ .......................... A61K 6/083; G08F 20/20; C08F 2/44
[52] U.S. Cl. .......................... 523/116; 524/236; 524/413; 524/783; 424/52; 433/228.1; 523/114
[58] Field of Search ..................... 523/116, 114; 524/236, 413, 783; 424/52; 428/228.1

[56] References Cited

U.S. PATENT DOCUMENTS

| 4,714,721 | 12/1987 | Franek et al. ........................... 523/113 |
| 4,746,686 | 5/1988 | Waller ........................................ 522/14 |
| 4,767,798 | 8/1988 | Gasser et al. ........................... 524/413 |
| 4,772,325 | 9/1988 | Kwan et al. ............................... 106/35 |
| 4,871,786 | 10/1989 | Aasen et al. ............................. 523/115 |
| 4,882,365 | 11/1989 | Gasser et al. ........................... 523/117 |
| 5,004,501 | 4/1991 | Faccioli et al. .......................... 523/116 |
| 5,037,638 | 8/1991 | Hamer et al. ............................ 523/116 |
| 5,154,762 | 10/1992 | Mitra et al. .............................. 523/116 |
| 5,304,586 | 4/1994 | Hammesfahr et al. ................. 523/116 |
| 5,527,836 | 6/1996 | Yamamuro et al. .................... 523/116 |

FOREIGN PATENT DOCUMENTS

| 0238025 | 9/1987 | European Pat. Off. . |
| 0373384 | 6/1990 | European Pat. Off. . |
| 0373385 | 6/1990 | European Pat. Off. . |
| 2954204 | 8/1979 | Germany . |
| 3404827 | 10/1984 | Germany . |
| 3609038 | 9/1987 | Germany . |
| 4032505 | 8/1991 | Germany . |
| 4104934 | 8/1992 | Germany . |

OTHER PUBLICATIONS

Japan Patent Information Organization, Ref. 88–130524 JP 63–130524, (1988).
CPI—Profile Booklet 1990, Ref. 90–087257/12 zu, JP 2–40310 A.

*Primary Examiner*—Andrew E. C. Merriam
*Attorney, Agent, or Firm*—Birch, Stewart, Kolasch & Birch, LLP

[57] ABSTRACT

The invention relates to fluoride-releasing, polymerizable dental composite materials having good mechanical stability, containing:

(a) one or more ethylenically unsaturated polymerizable monomers based on di- or multi-functional (meth) acrylates;

(b) initiators and optionally activators; and (c) usual fillers, and optionally pigments, thixotropic agents, plasticizers and other auxiliaries; and (d) one or more sufficiently water-soluble inorganic complex fluorides of the general formula $$A_n M F_m$$

wherein,

A is a monovalent cation, M is a metal of the III-V main group or II-V sub-group, n is a whole number from 1 to 3 and m is whole number from 3 to 6.

25 Claims, 2 Drawing Sheets

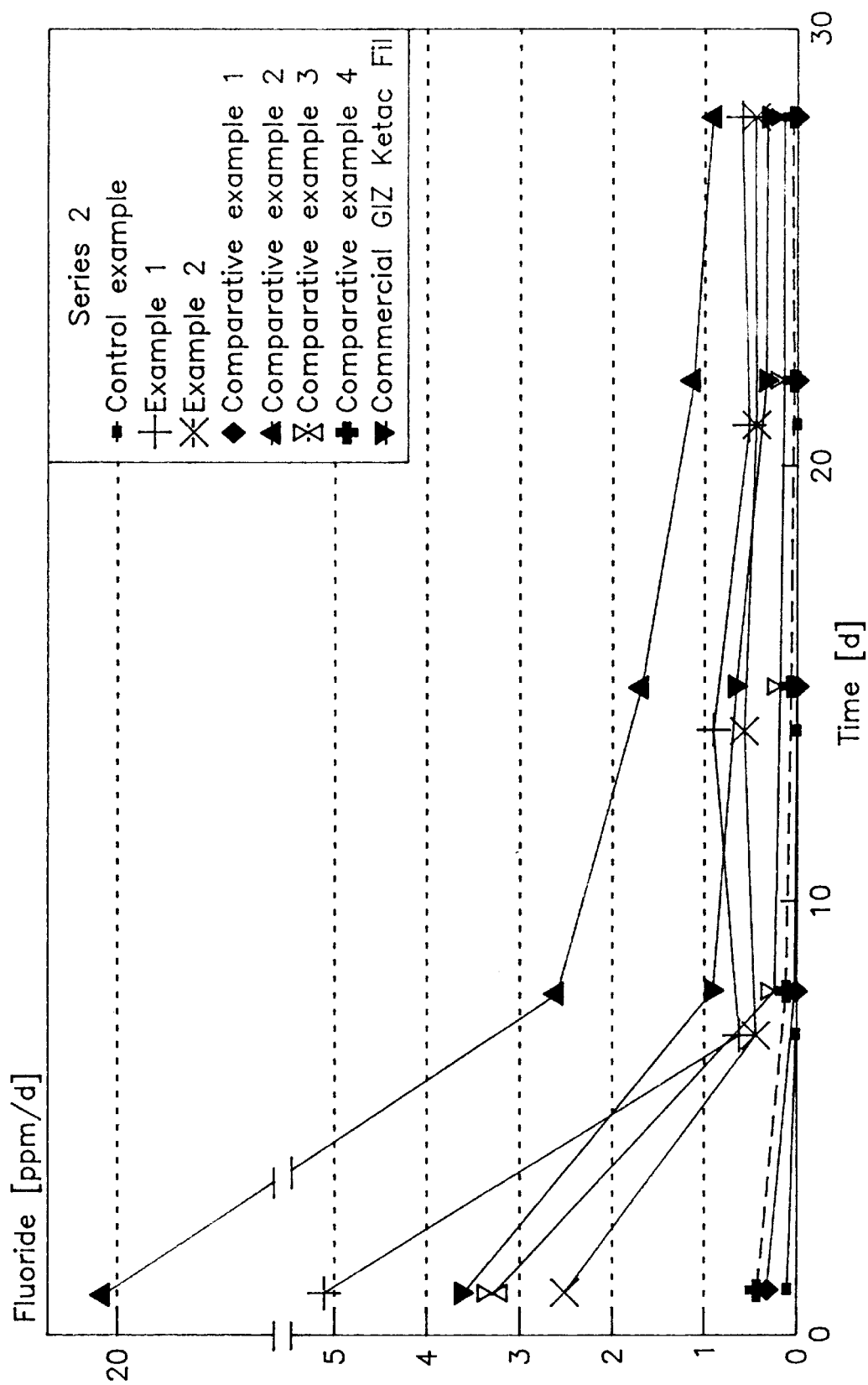

FLUORIDE-RELEASING COMPOSITE MATERIALS

BACKGROUND OF THE INVENTION

The formation of secondary caries on the edges of permanent dental fillings is a problem which has long been known in dental medicine. It has been shown that the tendency to form secondary caries in dental filling materials is reduced when they are able to release fluoride into the surrounding hard tooth substance. The reason for this is presumably the formation of caries-resistant fluorapatite by reaction of the hydroxylapatite in the tooth with released fluoride (R. S. Levine, "The Action of Fluoride in Caries Prevention", British Dental Journal 140 (1976) 9–14).

There is no agreement in the literature as regards the question of what quantity of fluoride has to be released from a filling material in order for it to provide a reliable caries-inhibiting action (R. W. Phillips, "Restorative Materials Containing Fluoride", Journal of American Dental Association 116 (1988) 762–763). In view of clinical findings with various fluoride-releasing filling materials, it is, however, to be noted that the quantity of fluoride which is released by glass ionomer cements can reduce the formation of secondary caries to an extent that is clinically relevant (G. Wesenberg et al., J. Oral Rehabil. 7 (1980) 175–184). Also, it has been shown that in the case of so-called composite filling materials that display no or very little fluoride release, there is a particular susceptibility to attack from secondary caries (E. A. M. Kidd, Br. Dent. J. 144 (1978) 139–142). As a result of shrinkage of the resin during curing, an edge gap can form which favors the formation of caries.

There has thus been no lack of attempts to prepare composite filling materials that display a fluoride ion release that is comparable with glass ionomer cements.

High release rates of fluoride are relatively easy to achieve in glass ionomer cements. The material that cures out because of a reaction of fluoride-containing glass and an aqueous polycarboxylic acid solution forms a hydrated cement in the solid state, which has ideal conditions for preparing and diffusing fluoride ions.

What is considerably more difficult to achieve is the release of fluoride from composite filling materials, which are also called resin fillings. In the cured form, composites essentially consist of a polymeric plastic matrix based on (meth)acrylate monomers and a high proportion of fillers. In order to protect the bond between plastic matrix and filler from the harmful effect of water (hydrolysis), composites are as a rule formulated to be non-polar and hydrophobic.

In contrast to the hydrous, hydrophilic matrix of glass ionomer cements, the hydrophobic matrix of composites prevents the release and diffusion of fluoride ions, however. Also, the introduction of fluoride-containing additives into composites is made difficult by the non-polarity and hydrophobic nature of these systems. This problem is described very vividly in B. F. Zimmermann et al., J. Dent. Res. 63 (1984) 689–692: "A major problem with incorporation of highly polar inorganic fluoride salts into low polarity polymer resins is phase separation and, consequently, loss of mechanical integrity . . . ."

U.S. Pat. No. 4,515,910 and U.S. Pat. No. 4,572,920 (Rawls et al.) describe polymers produced by the co-polymerization of fluoride-containing monomers with (meth)acrylates.

U.S. Pat. No. 5,037,638 (Hammer et al.) describes dental composites containing morpholinoethyl-methacryloyl-hydrofluoride (MEM HF) as a special fluoride-containing monomer that can be incorporated by polymerization. Introducing organic fluorides in quantities that effect a fluoride ion release similar to that for glass ionomer cement, does, however, weaken the polymer matrix. The high requirements as regards the mechanical stability of plastic fillers cannot be satisfied by such materials.

EP-B-0 238 025 (Gasser et al.) describes X-ray opaque polymerizable dental materials, containing yttrium fluoride and/or sparingly water soluble complex heavy metal fluorides, such as, e.g., barium hexafluoro-zirconate. These compounds serve exclusively to increase the X-ray opacity of the dental materials.

K. Aleksieva et al. (CA 103(6): 42608e) describe prosthesis plastics based on polymethyl methacrylate which contain sodium fluoride or potassium hexafluorotitanate. They found that, in contrast to sodium fluoride, potassium hexafluorotitanate weakens the tensile strength of the polymer. They come to the conclusion that the potassium hexafluorotitanate containing material is less well suited for producing dental prostheses than the sodium fluoride-containing material. In addition, sodium fluoride is known to be toxic.

SUMMARY OF THE INVENTION

It is an object of the present invention to provide a dental composite material that has a fluoride ion release comparable with glass ionomer cements, and which leads to permanent fillings with good mechanical stability.

This object is achieved by providing polymerizable dental materials, containing:

(a) one or more ethylenically unsaturated polymerizable monomers based on di- or multi-functional (meth)acrylates;

(b) initiators and, optionally, activators;

(c) usual fillers, and optionally, pigments, thixotropic auxiliaries, plasticizers and other auxiliaries; and that additionally contain therein (d) one or more sufficiently water-soluble inorganic complex fluorides of the general formula $$A_n MF_m$$

wherein,

A is a monovalent cation, M is a metal of the III-V main group or II-V sub-group of the periodic chart, n is a whole number from 1 to 3, and m is a whole number from 3 to 6.

A is preferably an alkali metal ion or $NR_4^+$, wherein R is a $C_1$–$C_{18}$ alkyl, phenyl or substituted phenyl.

The substituents for phenyl are preferably selected from the group consisting of $C_1$–$C_6$ alkyl groups, $C_1$–$C_6$ alkyl groups that are substituted by halides or nitrogen- or oxygen-containing groups, halides, $C_1$–$C_6$ alkoxy groups and $C_1$–$C_6$ alkyl amino groups.

A is particularly preferably a sodium or potassium ion, and R is particularly preferably $C_1$–$C_6$ alkyl.

$MF_m$ is preferably selected from $SiF_6^{2-}$, $TiF_6^{2-}$, $ZrF_6^{2-}$, $AlF_6^{3-}$, $ZnF_3^-$, $PF_6^-$ or $BF_4^-$, with $ZnF_3^-$ being particularly preferred.

BRIEF DESCRIPTION OF THE DRAWINGS

The present invention will become more fully understood from the detailed description given hereinbelow and the accompanying drawings which are given by way of illustration only, and, thus, are not limitative of the present invention.

FIG. 2 is a graphical representation of fluoride ion release from a second series of tested composite tooth-filling material without coloration. The fluoride ion release graphically shown in FIG. 2 is also summarized in Table 6.

DETAILED DESCRIPTION OF THE INVENTION

Figure 1:
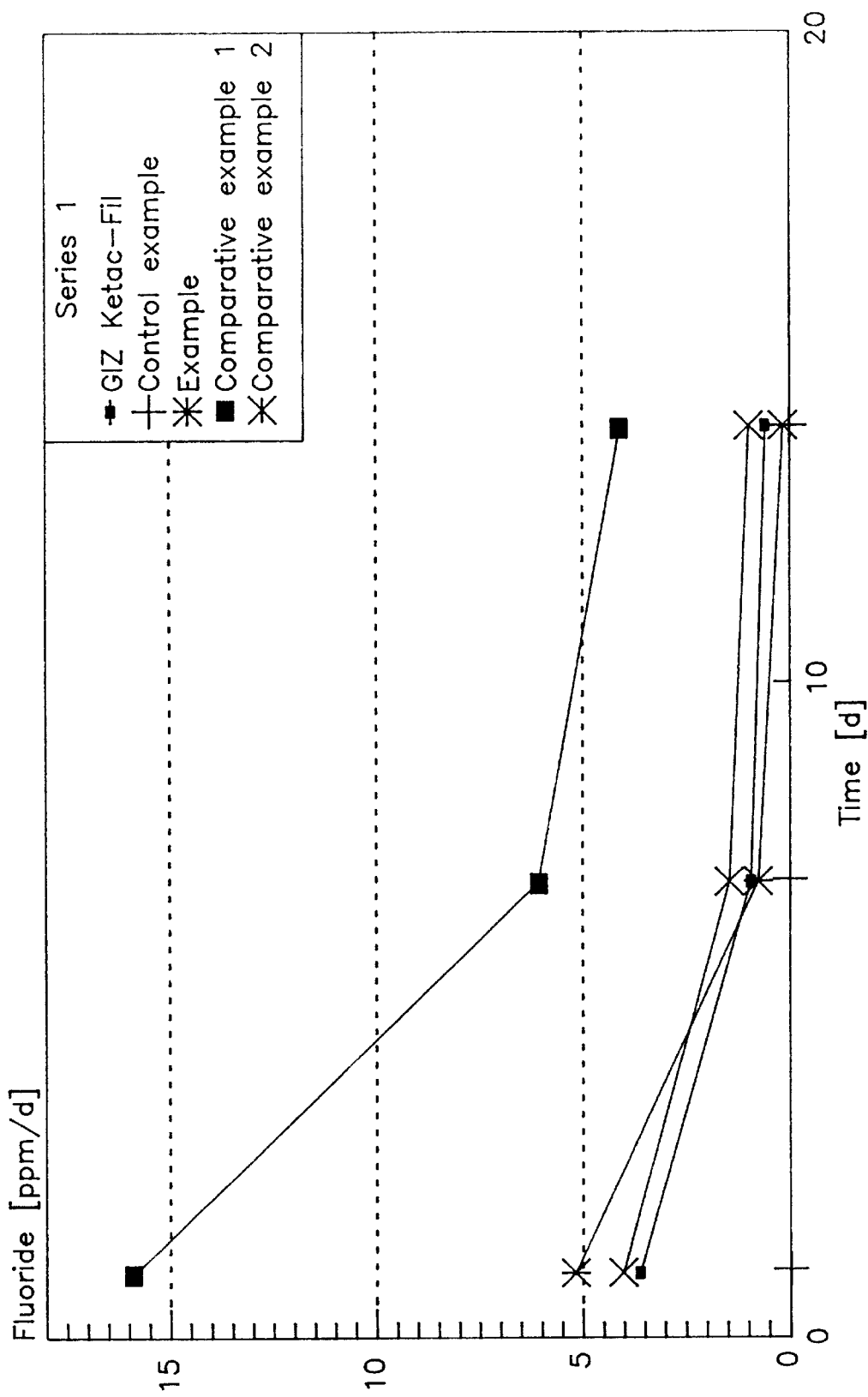
FIG. 1 is a graphical representation of fluoride ion release from a first series of tested composite tooth-filling materials possessing tooth-like coloration. The fluoride ion release graphically shown in FIG. 1 is also summarized in Table 2.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the inventive fluoride-releasing composite materials, the complex fluoride is contained therein in an amount of preferably 2 to 25% by wt., more preferably 5 to 15% by wt., and especially preferably 5 to 10% by wt., relative to the total weight of the material (components (a) to (d)).

The initiators and optional activators according to component (b) constitute 0.01 to 10% by wt., preferably 0.1 to 5% by wt. of the total weight (components (a) to (d)), and the fillers are contained in the materials according to the invention in an amount of preferably 40 to 85% by wt., and more preferably 50 to 80% by wt., relative to the total weight (components (a) to (d)).

The at least bifunctional acrylic acid and/or methacrylic acid esters to be used as constituent (a) according to the invention can contain monomeric and polymeric acrylates and methacrylates. The long-chained monomers of U.S. Pat. No. 3,066,112 based on bisphenol-A and glycidyl methacrylate or their derivatives resulting from addition of isocyanates can, for example, be advantageously used. Also suitable are compounds of the bisphenol-A-diethyloxy(meth) acrylate and bisphenol-A-dipropyloxy(meth)acrylate type. The oligo-ethoxylated and oligo-propoxylated bisphenol-A-diacrylic and dimethacrylic acid esters can also be used.

Also well suited are the acrylic acid and methacrylic acid esters of at least bifunctional aliphatic alcohols, for example triethylene glycol-di(meth)acrylate, ethylene glycol-di(meth)acrylate, hexanediol-di(meth)acrylate and trimethylol propane-tri(meth)acrylate.

Particularly suitable are also the diacrylic and dimethacrylic acid esters of bis(hydromethyl)-tricyclo (5.2.1.0$^{2,6}$) decane and the diacrylic and dimethacrylic acid esters of the compounds of biz(hydroxymethyl)tricyclo (5.2.1.0$^{2,6}$) decane extended with 1 to 3 ethylene oxide and/or propylene oxide units, as described in DE-C-2 816 823.

Well suited monomers are also the methacrylic acid esters described in EP-A-0 235 826, e.g., triglycolic acid bis(3(4)-methacryloyloxymethyl-8(9)-tricyclo(5.2.1.0$^{2,6}$)-decylmethyl esters).

Naturally, mixtures of monomers and/or of unsaturated polymers produced therefrom can also be used.

Suitable as constituent (b) are initiator systems that affect the radical polymerization of the at least bifunctional monomers, e.g., photoinitiators or so-called redox initiator systems.

Suitable as photoinitiators are, for example, α-diketones, such as camphor quinone, in conjunction with secondary and tertiary amines, or mono- and bisacyl phosphine oxides, such as 2,4,6-trimethyl benzoyl diphenyl phosphine oxide and bis(2,6-dichlorobenzoyl)-4-n-propylphenyl phosphine oxide. However, other compounds of this type are also suitable, as are described in European patent publication specifications EP-A-0 073 413, EP-A-0 007 508, EP-A-0 047 902, EP-A-0 057 474 and EP-A-0 184 095.

The concentration of the photoinitiators is in a particularly preferred manner 0.1 to 3% by wt., and more particularly 0.1 to 2% by wt., relative to the total weight of (a)+(b)+(c)+(d).

Suitable as redox initiator systems are organic peroxide compounds together with so-called activators. Coming into consideration as organic peroxide compounds are in particular compounds such as lauroyl peroxide, benzoyl peroxide and p-chlorobenzoyl peroxide and p-methyl benzoyl peroxide.

Suitable as activators are, for example, tertiary aromatic amines, such as the N,N-bis-(hydroxyalkyl)-3,5-xylidines known from U.S. Pat. No. 3,541,068 and the N,N-bis-(hydroxyalkyl)-3,5-di-t-butyl-anilines known from DE-A-2 658 530, particularly N,N-bis-(β-oxybutyl)-3,5-di-t-butyl-aniline and N,N-bis-(hydroxyalkyl) 3,4,5-trimethyl aniline.

Well suited activators are also the barbituric acids and barbituric acid derivatives described in DE-B-1 495 520 and the malonyl sulphamides described in EP-A-0 059 451. Preferred malonyl sulphamides are 2,6-dimethyl-4-isobutyl malonyl sulphamide, 2,6-diisobutyl-4-propyl malonyl sulphamide, 2,6-dibutyl-4-propyl malonyl sulphamide, 2,6-dimethyl-4-ethyl malonyl sulphamide and 2,6-dioctyl-4-isobutyl malonyl sulphamide.

For further acceleration, polymerization is preferably carried out in this case in the presence of heavy metal compounds and ionogenic halogen or pseudo-halogen. Copper is particularly suitable as a heavy metal, the chloride ion as a halide. The heavy metal is suitably used in the form of soluble organic compounds. Likewise, the halide and pseudo-halide ions are suitably used in the form of soluble salts, for example the soluble amine hydrochlorides and quaternary ammonium chloride compounds may be mentioned.

If the polymerizable dental materials according to the invention contain as (b) a redox initiator system of organic peroxide and activator, the peroxide and activator are preferably present in parts of the dental material according to the invention that are spatially separated from each other and homogeneously mixed together only directly prior to using the dental material according to the invention. If the dental material according to the invention contains organic peroxide, copper compound, halide and malonyl sulphamide alongside one another as (b), it is especially useful that organic peroxide, malonyl sulphamide and the combination of copper compound/halide are present in three constituents spatially separated from one another. For example, organic peroxide, polymerizable monomers and fillers can be kneaded to give a paste, and the other components can be kneaded in the manner described above in each case with a small quantity of fillers, or in particular thixotropic auxiliaries, such as silanized silica, and a plasticizer, for example phthalate, to give two separate pastes. On the other hand, the polymerizable monomers can also be present together with the copper compound/halide and fillers. Constituent (d) can, if the dental material according to the present invention is present in constituents spatially separated from one another, be present in each of these constituents.

Apart from the at least bifunctional acrylic acid and methacrylic acid esters (a) and the initiator system (b), up to 85% by wt., relative to the total weight of (a)+(b)+(c)+(d), of organic and/or inorganic fillers, pigments, dyes, thixotropic auxiliaries, plasticizers and other auxiliaries are contained in the inventive compositions.

Inorganic fillers can, for example, be quartz, ground glasses, non-water-soluble fluorides, such as $CaF_2$ or $SrF_2$, silica gels and silica, in particular pyrogenic silica or its granules. They are preferably contained in the dental materials in a concentration of 40 to 85% by wt., quite particularly preferably 50 to 80% by wt., relative to the total weight of (a)+(b)+(c)+(d). For better incorporation into the polymer matrix, it can be advantageous to make the fillers and optionally X-ray opaque additives hydrophobic. In a preferred embodiment, all the inorganic fillers used are silanized, preferably with trimethoxymethacryloxypropyl silane. The quantity of silane used is usually 0.5 to 10% by wt., relative to inorganic fillers, preferably 1 to 6%, and quite particularly preferably 2 to 5% by, wt., relative to inorganic fillers. Usual hydrophobing agents are silanes, for example trimethoxymethacryloxypropyl silane. The maximum average grain size of the inorganic fillers is preferably 15 µm, in particular preferably 8 µm. Quite especially preferably used are fillers with an average grain size of less than 3 µm.

Suitable as fillers are also ready-pigmented polymethyl methacrylate beads or other pulverized organic polymers. To increase the flexibility of the materials it can also be advantageous to use soluble organic polymers. Suitable are, e.g., polyvinyl acetate and the copolymers based on vinyl chloride/vinyl acetate, vinyl chloride/vinyl isobutyl ether and vinyl acetate/maleic acid dibutyl ether. Well suited as additional plasticizers are for example dibutyl, dioctyl and dinonylphthalates.

The materials according to the invention can be used inter alia as permanent filling materials, sealing materials, cements or as materials for temporary fillings or crowns and bridges.

The polymerizable fluoride-releasing dental materials according to the invention have good mechanical values (compressive and bending strengths), good long-term stability of the cured material and excellent aesthetics. Their fluoride ion release is comparable with that of a standard commercial glass ionomer cement.

EXAMPLES

Series 1:
Preparation and testing of conventional and fluoride-releasing composite tooth-filling materials with tooth-like coloration.
Preparation of a Pre-mix
A pre-mix is kneaded from 70 parts by weight bis-acryloxymethyltricyclo(2.5.1.0$^{2,6}$) -decane and 30 parts by weight 2,2-bis-4-(3-methacryloxypropoxy)-phenyl propane (modified bis-GMA), 24 parts by weight silanized pyrogenic silica, 0.3 parts by weight camphor quinone, 3 parts by weight N-dimethyl aminoethyl methacrylate and 110 parts by weight $YF_3$.
Control Example
3.9 g of the pre-mix and 6.1 g silanized tooth-like pigmented quartz (grain upper limit approx. 3 µm, average grain size approx. 1.5 µm) are kneaded to give a conventional tooth-filling material with a uniformly pasty consistency.
Example and Comparative Example 1
3.9 g of the pre-mix are treated, for the paste according to the invention with 1.6 g pulverized potassium hexafluorotitanate and, for the comparative paste with 1.6 g pulverized sodium fluoride, and in each case 4.5 g of silanized, tooth-like pigmented quartz (average grain size 1.5 µm) to give a tooth-filling material with a uniformly pasty consistency.

Comparative Example 2
3.9 g of the pre-mix are treated with 0.4 g pulverized sodium fluoride and 5.7 g silanized tooth-like pigmented quartz (average grain size 1.5 µm) to give a tooth-filling composition with a uniformly pasty consistency.

The tooth-colored pastes of the Control Example, of the Example according to the invention, and of Comparative Examples 1 to 2, were molded and cured to give test pieces. The compressive strength, the bending strength and the opacity of the test pieces were then determined. The results of the investigations are summarized in Table 1 below.

TABLE 1

Mechanical properties of the cured tooth-colored composites (Series 1: Control Example, Example and Comparative Examples 1 and 2).

|  | Control Example | Example | Comparative Example 1 | Comparative Example 2 |
| --- | --- | --- | --- | --- |
| Compressive Strength[1] [MPa] | 420 | 410 | 340 | 360 |
| Bending Strength[2] [MPa] | 110 | 102 | 87 | 90 |
| Opacity[3] [%] | 92.0 | 93.3 | 99.8 | 98.0 |

[1] Compressive strength measured according to ISO 9917
[2] Bending strength measured according to ISO 4049
[3] Opacity measured with a CIELAB colorimeter (Testpiece disks diameter 2 cm, height 3.5 mm)

In further investigations, the fluoride ion release of the cured tooth-colored composites of the Control Example, of the Example according to the invention, of Comparative Examples 1 and 2, and of a standard commercial glass ionomer cement (GIZ KETAC-FIL) was determined.

The results are summarized in Table 2 below, and are represented graphically in FIG. 1. The fluoride ion release of the inventive example is surprisingly high and comparable with that of the standard commercial glass ionomer cement.

TABLE 2

Fluoride release[1] of the composites of Series 1 (ppm F/d).

|  | 1 Day | 7 Days | 14 Days |
| --- | --- | --- | --- |
| GIZ Ketac-Fil | 3.60 | 1.00 | 0.62 |
| Control Example | 0.05 | 0.01 | 0.01 |
| Example | 5.16 | 0.82 | 0.19 |
| Comparative Example 1 | 15.90 | 6.00 | 4.10 |
| Comparative Example 2 | 4.00 | 1.50 | 1.00 |

[1] Two test pieces (diameter 15 mm, h 1.5 mm) are stored freely suspended in 50 ml distilled water at 36°C. and, after the appropriate period, the fluoride concentration is measured using ion-sensitive electrodes. After each measurement the water is changed. The data refer to the daily release.

Series 2:
Preparation and testing of conventional and fluoride-releasing composite tooth-filling materials without coloration.
Preparation of a Pre-mix
A pre-mix is kneaded from 70 parts by weight bis-acryloxymethyltricyclo(2.5.1.0$^{2,6}$) -decane and 30 parts by weight 2,2-bis-4-(3-methacryloxypropoxy)-phenyl propane 24 parts by weight silanized pyrogenic silica, 0.3 parts by weight camphor quinone, 3 parts by weight N-dimethylaminoethyl methacrylate and 110 parts by weight $YF_3$.

Preparation of the Composite Pastes

The quantity of pre-mix given in Table 3 is treated in each case with the given quantities of fluoride-releasing filler and non-pigmented quartz to give tooth-filling materials of comparable pasty consistency. The consistency is controlled with reference to the viscosity.

Properties of the Composites

Table 3 shows the compositions of Examples 1 and 2 and of the control example and of comparative examples 1 to 4 of Series 2. At a comparable content of fluoride-releasing filler and comparable viscosity (processing properties), the composites according to the invention have an increased total filler content. As a result, the polymerization shrinkage attributable to the plastic matrix is reduced compared with less filled systems (cf. Table 4). This can counteract the tendency towards edge gap formation.

Table 4 shows that the composites according to the invention also. have good aesthetics (=low opacity) in addition to excellent mechanical values in the non-colored state. Compared with the materials with sodium fluoride (Comparative Examples 2 and 3), which appear dull and lifeless, the materials according to the invention have partly tooth-like transparency and aesthetics.

In particular, the comparison of the $K_2TiF_6$ with the NaF-containing materials is surprising. K. Aleksieva et al. report that NaF as a fluoride-releasing constituent weakens the mechanical values of PMMA prosthesis plastics significantly less than $K_2TiF_6$. Unexpectedly, the opposite is found for the composite materials based on difunctional (meth) acrylates.

Table 5 shows that in a hydrolysis stability test (10 h storage in water at 100° C.) the surface hardness of the materials according to the invention increases in a clearly more marked manner (so-called secondary curing effect) than in the case of the comparative examples.

Table 6 gives an overview of the fluoride release from the composites. FIG. 2 shows this graphically. With the composites according to the invention, release rates are achieved that are comparable with commercially obtainable glass ionomer cements (e.g. KETAC-FIL, ESPE, Seefeld). With NaF as a fluoride-releasing filler (see Comparative Example 2), yet higher release rates are of course possible in principle but, because of the poor mechanical values and the deficient aesthetics (cf. Tables 3 and 4), NaF-containing materials are clearly inferior to the composites according to the invention.

The preparations according to the invention thus permit the formulation of composites as dental materials that well satisfy the following requirements:

Fluoride release comparable to glass ionomer cements,

Good mechanical values,

Excellent aesthetics,

High stability in an aqueous medium, and which thus represent a significant improvement compared with the state of the art.

TABLE 3

Composition of the Composites from Series 2

| | Fluoride-Releasing Filler | Fluoride-Releasing Filler [g] | Pre-mix [g] | Non-Pigmented Quartz [g] | Total Filler Content [%][1] | Viscosity[3] [mm] |
|---|---|---|---|---|---|---|
| Control Example | — | 0 | 42.9 | 57.1 | 81.0 | 0.65 |
| Example 1 | $K_2TiF_6$ | 15.0 | 36.5 | 48.5 | 83.8 | 0.65 |
| Example 2 | $KZnF_3$ | 15.3 | 37.1 | 47.6 | 83.6 | 0.82 |
| Comparative Example 1 | $BaZrF_6$ | 15.9 | 38.5 | 45.6 | 83.0 | 0.98 |
| Comparative Example 2 | NaF | 15.0 | 47.5 | 37.5 | 78.9 | 1.12 |
| Comparative Example 3 | NaF | 4.0 | 47.2 | 48.8 | 79.1 | 0.62 |
| Comparative Example 4 | MEM HF | 3.6 | 36.7 | 59.7 | 80.1[2] | 0.68 |

[1]Total filler content = Σ(amount of filler in the pre-mix + quartz + fluoride-releasing filler).
[2]MEM HP is a liquid, its amount is not included in the fillers.
[3]Measurement of the viscosity by "extrusion compression": 0.6 g of the paste in the form of an extrudate of 4 mm diameter is loaded with 200 g between two plates for 60 s. After 60 s the distance between the two plates is measured.

TABLE 4

Mechanical Values of the Composites from Series 2

| | Fluoride-Releasing Filler | Content [%] | Compressive Strength [MPa] | Bending Strength [MPa] | Volume Shrinkage [%] | Opacity [%] |
|---|---|---|---|---|---|---|
| Control Example | — | 0 | 474 | 146 | 2.53 | 76.4 |
| Example 1 | $K_2TiF_6$ | 15.0 | 438 | 127 | 2.12 | 81.1 |
| Example 2 | $KZnF_3$ | 15.3 | 464 | 121 | 1.81 | 89.0 |
| Comparative Example 1 | $BaZrF_6$ | 15.9 | 441 | 127 | 1.92 | 81.2 |
| Comparative Example 2 | NaF | 15.0 | 348 | 93 | 1.31 | 98.5 |
| Comparative Example 3 | NaF | 4.0 | 422 | 106 | 2.24 | 90.3 |
| Comparative Example 4 | MEM HF | 3.6 | 416 | 112 | 2.39 | 78.4 |

TABLE 5

Surface Hardness of the Composites from Series 2 Before and After Storage in Water for 10 h at 100° C.

| | Surface Hardness [MPa] | | |
|---|---|---|---|
| | Before | After | Change |
| Control Example | 383 | 547 | +43% |
| Example 1 | 478 | 765 | +60% |
| Example 2 | 479 | 638 | +33% |
| Comparative Example 1 | 479 | 638 | +33% |
| Comparative Example 2 | 166 | 174 | +5% |
| Comparative Example 3 | 383 | 383 | ±0% |
| Comparative Example 4 | 383 | 383 | ±0% |

TABLE 6

Fluoride Release[1]) of the Composites from Series 2 [ppm F/d]

| | Fluoride Release [ppm/d][1]) | | | | |
|---|---|---|---|---|---|
| | 1 Day | 1 Week | 2 Weeks | 3 Weeks | 4 Weeks |
| Control Example | <0.1 | <0.01 | <0.01 | <0.01 | <0.01 |
| Example 1 | 5.1 | 0.59 | 0.89 | 0.51 | 0.59 |
| Example 2 | 2.5 | 0.42 | 0.57 | 0.44 | 0.46 |
| Comparative Example 1 | 0.3 | 0.04 | 0.03 | 0.01 | 0.02 |
| Comparative Example 2 | 20.5 | 2.64 | 1.71 | 1.14 | 0.92 |
| Comparative Example 3 | 3.3 | 0.17 | 0.16 | 0.13 | 0.13 |
| Comparative Example 4 | 0.4 | 0.11 | 0.07 | 0.06 | 0.05 |
| Commercial glass ionomer cement "Ketac Fil" (ESPE, Seefeld) | 3.6 | 0.87 | 0.63 | 0.3 | 0.27 |

[1])Two test pieces (diameter 15 mm, h 1.5 mm) are stored freely suspended in 50 ml distilled water at 36° C., and after the appropriate period, the fluoride concentration in the water is measured using ion-sensitive electrodes and converted to the quantity released daily. After each measurement, the water is changed.

The invention thus being described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A polymerizable dental material, comprising:
   (a) one or more ethylenically unsaturated polymerizable monomers selected from the group consisting of di- and multi-functional (meth)acrylates;
   (b) initiators and optionally activators;
   (c) usual fillers, and optionally pigments, thixotropic auxiliaries, plasticizers and other auxiliaries; and
   (d) one or more sufficiently water-soluble inorganic complex fluorides of the following formula $$A_n MF_m$$

wherein,
   A is an alkali metal ion or $NR_4^+$, with R being $C_1$–$C_{18}$ alkyl, phenyl or substituted phenyl,
   M is a metal of the IIIA-VA group or IIB-VB group, with the proviso that M is not silicon or boron,
   n is a whole number from 1 to 3, and
   m is a whole number from 3 to 6.

2. The dental material according to claim 1, wherein R is a substituted phenyl and the substituents for phenyl are selected from the group consisting of $C_1$–$C_6$ alkyl groups, $C_1$–$C_6$ alkyl groups that are substituted by halides or nitrogen- or oxygen-containing groups, halides, $C_1$–$C_6$ alkoxy groups and $C_1$–$C_6$ alkyl amino groups.

3. The dental material according to claim 1, wherein R is a $C_1$–$C_6$ alkyl group.

4. The dental material according to claim 1, wherein the group $MF_m$ is $TiF_6^{2-}$, $ZrF_6^{2-}$, $AlF_6^{3-}$, $ZnF_3^-$ or $PF_6^-$.

5. The dental material according to claim 1, containing:
   10 to 55% by weight of component (a),
   0.01 to 10% by weight of component (b),
   40 to 85% by weight of component (c), and
   2 to 25% by weight of component (d).

6. The dental material according to claim 1, containing:
   14 to 44% by weight of component (a),
   0.1 to 5% by weight of component (b),
   50 to 80% by weight of component (c), and
   5 to 15% by weight of component (d).

7. The dental material according to claim 1, containing:
   14 to 44% by weight of component (a),
   0.1 to 5% by weight of component (b),
   50 to 80% by weight of component (c), and
   5 to 10% by weight of component (d).

8. In a method of producing a fluoride-releasing dental material, the improvement which comprises:
   preparing a polymerizable composite that contains
   (a) one or more ethylenically unsaturated polymerizable monomers selected from the group consisting of di- or multi-functional (meth)acrylates,
   (b) initiators and optionally activators,
   (c) usual fillers, and optionally pigments, thixotropic auxiliaries, plasticizers and other auxiliaries, and
   (d) one or more sufficiently water-soluble inorganic complex fluorides of the following formula $$A_n MF_m$$

wherein,
   A is a monovalent cation,
   M is a metal of the IIIA-VA group or IIB-VB group, with the proviso that m is not boron or silicon,
   n is a whole number from 1 to 3, and
   m is a whole number from 3 to 6.

9. The method of claim 8, wherein A is an alkali metal ion or $NR_4^+$, with R being $C_1$–$C_{18}$ alkyl, phenyl or substituted phenyl.

10. The method of claim 9, wherein R is substituted phenyl and the substituents for phenyl are selected from the group consisting of $C_1$–$C_6$ alkyl groups, $C_1$–$C_6$ alkyl groups that are substituted by halides or nitrogen- or oxygen-containing groups, halides, $C_1$–$C_6$ alkoxy groups and $C_1$–$C_6$ alkyl amino groups.

11. The method of claim 9, wherein R is a $C_1$–$C_6$ alkyl group.

12. The method of claim 8, wherein the group $MF_m$ is $TiF_6^{2-}$, $ZrF_6^{2-}$, $AlF_6^{3-}$, $ZnF_3^-$ or $PF_6^-$.

13. The method of claim 8, wherein the dental material is selected from the group consisting of a permanent dental-filling material, a temporary dental-filling material, a dental crown, a provisional dental crown, a dental bridge, a provisional dental bridge and a dental cement.

14. A method of producing a fluoride-releasing composite, which comprises:

(i) preparing a polymerizable composite that contains
 (a) one or more ethylenically unsaturated polymerizable monomers selected from the group consisting of di- or multi-functional (meth)acrylates,
 (b) initiators and optionally activators,
 (c) usual fillers, and optionally pigments, thixotropic auxiliaries, plasticizers and other auxiliaries, and
 (d) one or more sufficiently water-soluble inorganic complex fluorides of the following formula $$A_nMF_m$$

wherein,
 A is a monovalent cation, M is a metal of the IIIA-VA group or IIB-VB group, with the proviso that m is not boron or silicon,
 n is a whole number from 1 to 3, and
 m is a whole number from 3 to 6; and
(ii) polymerizing said polymerizable composite.

15. The method of claim 14, wherein A is an alkali metal ion or $NR_4^+$, with R being $C_1$–$C_{18}$ alkyl, phenyl or substituted phenyl.

16. The method of claim 15, wherein R is a substituted phenyl and the substituents for phenyl are selected from the group consisting of $C_1$–$C_6$ alkyl groups, $C_1$–$C_6$ alkyl groups that are substituted by halides or nitrogen- or oxygen-containing groups, halides, $C_1$–$C_6$ alkoxy groups and $C_1$–$C_6$ alkyl amino groups.

17. The method of claim 15, wherein R is a $C_1$–$C_6$ alkyl group.

18. The method of claim 14, wherein the group $MF_m$ is $TiF_6^{2-}$, $ZrF_6^{2-}$, $AlF_6^{3-}$, $ZnF_3^-$ or $PF_6^-$.

19. The method of claim 14, wherein the dental material is selected from the group consisting of a permanent dental-filling material, a temporary dental-filling material, a dental crown, a provisional dental crown, a dental bridge, a provisional dental bridge and a dental cement.

20. A polymerizable dental material, comprising:
 (a) one or more ethylenically unsaturated polymerizable monomers selected from the group consisting of di- or multi-functional (meth)acrylates;
 (b) initiators and optionally activators;
 (c) usual fillers, and optionally pigments, thixotropic auxiliaries, plasticizers and other auxiliaries; and
 (d) one or more sufficiently water-soluble inorganic complex fluorides of the following formula $$A_nMF_m$$

wherein,
 A is a monovalent cation,
 M is a metal of the IIIA-VA group or IIB-VB group, with the proviso that M is not boron,
 n is a whole number from 1 to 3, and
 m is a whole number from 3 to 6.

21. The dental material according to claim 20, wherein the group $MF_m$ is $SiF_6^{-2}$.

22. In a method of producing a fluoride-releasing dental material, the improvement which comprises:
preparing a polymerizable composite that contains
 (a) one or more ethylenically unsaturated polymerizable monomers selected from the group consisting of di- or multi-functional (meth)acrylates,
 (b) initiators and optionally activators,
 (c) usual fillers, and optionally pigments, thixotropic auxiliaries, plasticizers and other auxiliaries, and
 (d) one or more sufficiently water-soluble inorganic complex fluorides of the following formula $$A_nMF_m$$

wherein,
 A is a monovalent cation,
 M is a metal of the IIIA-VA group or IIB-VB group, with the proviso that m is not boron,
 n is a whole number from 1 to 3, and
 m is a whole number from 3 to 6.

23. The method of claim 22, wherein the $MF_m$ group is $SiF_6^{2-}$.

24. A method of producing a fluoride-releasing composite, which comprises:
 (i) preparing a polymerizable composite that contains
  (a) one or more ethylenically unsaturated polymerizable monomers selected from the group consisting of di- or multi-functional (meth)acrylates,
  (b) initiators and optionally activators,
  (c) usual fillers, and optionally pigments, thixotropic auxiliaries, plasticizers and other auxiliaries, and
  (d) one or more sufficiently water-soluble inorganic complex fluorides of the following formula $$A_nMF_m$$

wherein,
 A is a monovalent cation, M is a metal of the IIIA-VA group or IIB-VB group, with the proviso that m is not boron or silicon,
 n is a whole number from 1 to 3, and
 m is a whole number from 3 to 6; and
(ii) polymerizing said polymerizable composite.

25. The method of claim 24, wherein the $MF_m$ group is $SiF_6^{2-}$.

* * * * *